US012593962B2

(12) United States Patent
Sasai

(10) Patent No.: US 12,593,962 B2
(45) Date of Patent: Apr. 7, 2026

(54) ENDOSCOPE SYSTEM AND COORDINATE SYSTEM CORRECTION METHOD

(71) Applicant: OLYMPUS CORPORATION, Tokyo (JP)

(72) Inventor: Ryota Sasai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 202 days.

(21) Appl. No.: 18/610,966

(22) Filed: Mar. 20, 2024

(65) Prior Publication Data

US 2024/0225424 A1 Jul. 11, 2024

Related U.S. Application Data

(63) Continuation of application No. PCT/JP2021/043828, filed on Nov. 30, 2021.

(51) Int. Cl.
*A61B 1/00* (2006.01)
*G06T 7/246* (2017.01)
(Continued)

(52) U.S. Cl.
CPC .... *A61B 1/00149* (2013.01); *A61B 1/000095* (2022.02); *A61B 1/00042* (2022.02);
(Continued)

(58) Field of Classification Search
CPC .......... A61B 1/00149; A61B 1/000095; A61B 1/00042; A61B 1/00177; A61B 1/00193;
(Continued)

(56) References Cited

U.S. PATENT DOCUMENTS 9,188,973 B2 11/2015 Tenney et al.
12,175,556 B2 * 12/2024 Terry ..................... A61B 90/25
(Continued)

FOREIGN PATENT DOCUMENTS

EP 3 566 672 A1 11/2019
JP 3236070 B2 12/2001
(Continued)

OTHER PUBLICATIONS

International Search Report dated Feb. 15, 2022 received in PCT/JP2021/043828.

*Primary Examiner* — John R Schnurr
(74) *Attorney, Agent, or Firm* — Scully, Scott, Murphy & Presser, P.C.

(57) ABSTRACT

An endoscope system includes: an endoscope; a moving device that holds and moves the endoscope; and at least one processor. The at least one processor is configured to: detect a movement direction of the endoscope moved by the moving device in a coordinate system of the moving device; estimate an area of a moving body in an image captured by the endoscope; detect a movement direction of an object in the image on the basis of another area in the image excluding the area of the moving body; calculate a deviation between a coordinate system of the endoscope and the coordinate system of the moving device on the basis of the movement direction of the endoscope and the movement direction of the object; and correct the coordinate system of the moving device on the basis of the deviation.

20 Claims, 10 Drawing Sheets

(51) Int. Cl.
    *G06T 7/73*          (2017.01)
    *H04N 23/50*      (2023.01)

(52) U.S. Cl.
    CPC ...... *A61B 1/00177* (2013.01); *A61B 1/00193* (2013.01); *G06T 7/248* (2017.01); *G06T 7/74* (2017.01); *G06T 2200/24* (2013.01); *G06T 2207/10012* (2013.01); *G06T 2207/10068* (2013.01); *G06T 2207/30004* (2013.01); *H04N 23/555* (2023.01)

(58) Field of Classification Search
    CPC ...... A61B 2034/2065; A61B 2034/301; A61B 2090/3612; A61B 1/00009; A61B 34/30; A61B 1/00179; G06T 7/248; G06T 7/74; G06T 2200/24; G06T 2207/10012; G06T 2207/10068; G06T 2207/30004; G06T 7/269; H04N 23/555
    See application file for complete search history.

(56)             References Cited

U.S. PATENT DOCUMENTS

| | | | |
|---|---|---|---|
| 12,415,280 B2 * | 9/2025 | Ding | B25J 9/1692 |
| 12,446,969 B2 * | 10/2025 | Sexson | A61B 34/35 |
| 2009/0088634 A1 * | 4/2009 | Zhao | A61B 1/00193 600/425 |
| 2013/0010081 A1 * | 1/2013 | Tenney | H04N 13/20 348/47 |
| 2016/0035079 A1 | 2/2016 | Tenney et al. | |
| 2017/0165013 A1 * | 6/2017 | Itkowitz | A61B 34/37 |
| 2018/0049810 A1 * | 2/2018 | Besser | A61B 5/742 |
| 2019/0110843 A1 * | 4/2019 | Ummalaneni | A61B 1/000094 |
| 2019/0167079 A1 * | 6/2019 | Inoue | A61B 34/30 |
| 2020/0110956 A1 * | 4/2020 | Fan | H04N 21/42204 |
| 2020/0121399 A1 * | 4/2020 | Besser | A61M 25/0158 |
| 2022/0079706 A1 * | 3/2022 | Yuan | A61B 90/37 |
| 2022/0117675 A1 * | 4/2022 | Besser | A61B 5/0033 |
| 2022/0160214 A1 | 5/2022 | Yasuda et al. | |
| 2022/0192701 A1 * | 6/2022 | Junio | A61B 17/34 |
| 2022/0217286 A1 | 7/2022 | Osborne et al. | |
| 2022/0218426 A1 | 7/2022 | Itkowitz et al. | |
| 2023/0026537 A1 * | 1/2023 | Sasai | A61B 8/08 |
| 2023/0157777 A1 * | 5/2023 | Cheon | A61B 1/0016 600/102 |
| 2023/0172675 A1 * | 6/2023 | Ogimoto | G06T 7/70 600/102 |
| 2023/0320793 A1 * | 10/2023 | Yanagihara | G06T 7/0012 348/74 |
| 2024/0324847 A1 * | 10/2024 | Tajima | A61B 1/00 |
| 2024/0389830 A1 * | 11/2024 | Sasai | A61B 1/00149 |

FOREIGN PATENT DOCUMENTS

| | | |
|---|---|---|
| JP | 2014-520351 A | 8/2014 |
| JP | 2017-515523 A | 6/2017 |
| JP | 2020-162633 A | 10/2020 |
| WO | 2013/009510 A2 | 1/2013 |
| WO | 2015/142956 A1 | 9/2015 |

\* cited by examiner

ROTATE ABOUT Xbase AXIS BY $\theta$

ROTATE ABOUT Y1 AXIS BY $\alpha$

ROTATE ABOUT X2 AXIS BY $\beta$

| DIRECTION | d1 | d2 | d3 | d4 | d5 | d6 |
|---|---|---|---|---|---|---|
| NUMBER | n1 | n2 | n3 | n4 | n5 | n6 |

ENDOSCOPE SYSTEM AND COORDINATE SYSTEM CORRECTION METHOD

CROSS-REFERENCE TO RELATED APPLICATIONS

This is a continuation of International Application PCT/JP2021/043828 which is hereby incorporated by reference herein in its entirety.

TECHNICAL FIELD

The present invention relates to an endoscope system and a coordinate system correction method.

BACKGROUND ART

In a conventionally known endoscope system, an endoscope is moved by a moving device such as an electric holder. In order to move the endoscope accurately, it is desirable that the coordinate system of the endoscope and the coordinate system of the moving device coincide with each other.

For example, when an operator remotely operates the electric holder using a user interface, the operator inputs a desired movement direction of the endoscope to the user interface on the basis of the endoscopic image. When the coordinate system of the endoscope and the coordinate system of the moving device coincide with each other, the user can intuitively and accurately move the endoscope in the desired direction. In contrast, when the coordinate system of the endoscope and the coordinate system of the moving device do not coincide with each other, the actual movement direction of the endoscope differs from the movement direction input to the user interface. Hence, it is difficult for the user to intuitively and accurately move the endoscope in the desired direction.

Meanwhile, in a robot system in which a camera system is attached to a movable arm, a method for correcting transformation between the coordinate system of a robot and the coordinate system of the camera system is known (for example, see PTL 1). In PTL 1, an image of a target is acquired with the camera system, and the transformation is determined from the position of the movable arm and the position of a feature point of the target in the image when the image is acquired.

CITATION LIST

Patent Literature (PTL 1) U.S. Pat. No. 9,188,973

SUMMARY OF INVENTION

An aspect of the present invention is an endoscope system including: an endoscope; a moving device that holds and moves the endoscope; and at least one processor. The at least one processor is configured to: detect a movement direction of the endoscope moved by the moving device in a coordinate system of the moving device; estimate an area of a moving body in an image captured by the endoscope; detect a movement direction of an object in the image on the basis of another area in the image excluding the area of the moving body; calculate a deviation between a coordinate system of the endoscope and the coordinate system of the moving device on the basis of the movement direction of the endoscope and the movement direction of the object; and correct the coordinate system of the moving device on the basis of the calculated deviation.

Another aspect of the invention is an endoscope system including: an endoscope; a moving device that holds and moves the endoscope; and at least one processor. The at least one processor is configured to: detect a movement direction of the endoscope moved by the moving device in a coordinate system of the moving device; estimate motion vectors at respective positions in an image captured by the endoscope; detect a movement direction of an object in the image on the basis of another area in the image excluding an area in which magnitudes of the motion vectors are greater than or equal to a predetermined threshold; calculate a deviation between a coordinate system of the endoscope and the coordinate system of the moving device on the basis of the movement direction of the endoscope and the movement direction of the object; and correct the coordinate system of the moving device on the basis of the calculated deviation.

Another aspect of the invention is a coordinate system correction method for correcting a coordinate system of a moving device that holds and moves an endoscope, the method comprising: detecting a movement direction of the endoscope moved by the moving device in the coordinate system of the moving device; estimating an area of a moving body in an image captured by the endoscope; detecting a movement direction of an object in the image on the basis of another area in the image excluding the area of the moving body; calculating a deviation between a coordinate system of the endoscope and the coordinate system of the moving device on the basis of the movement direction of the endoscope and the movement direction of the object; and correcting the coordinate system of the moving device on the basis of the calculated deviation.

DESCRIPTION OF EMBODIMENTS

First Embodiment

An endoscope system and a coordinate system correction method according to a first embodiment of the present invention will be described with reference to the drawings.

Figure 1:
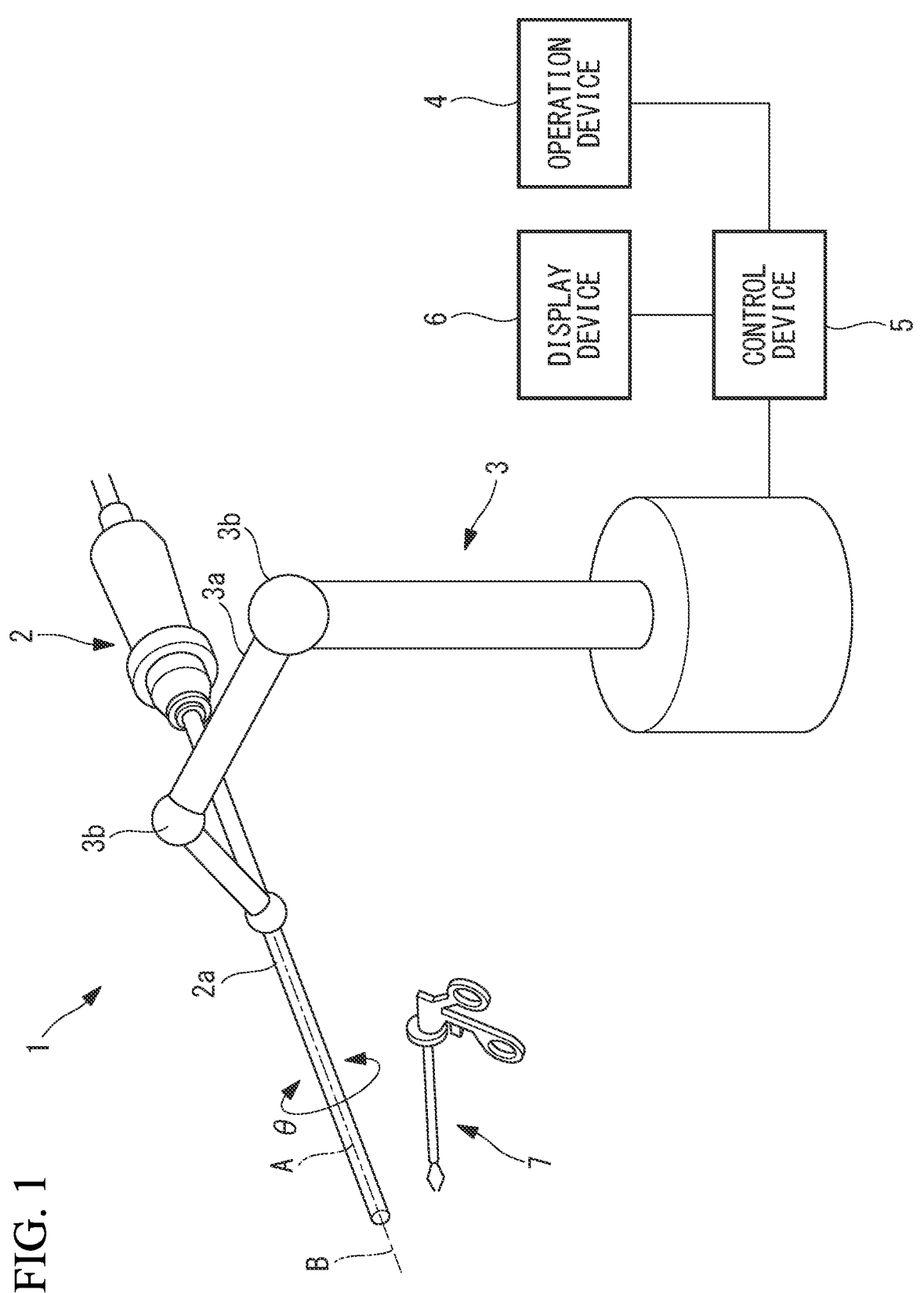
FIG. 1 illustrates the overall configuration of an endoscope system according to a first embodiment of the present invention.
Figure 2:
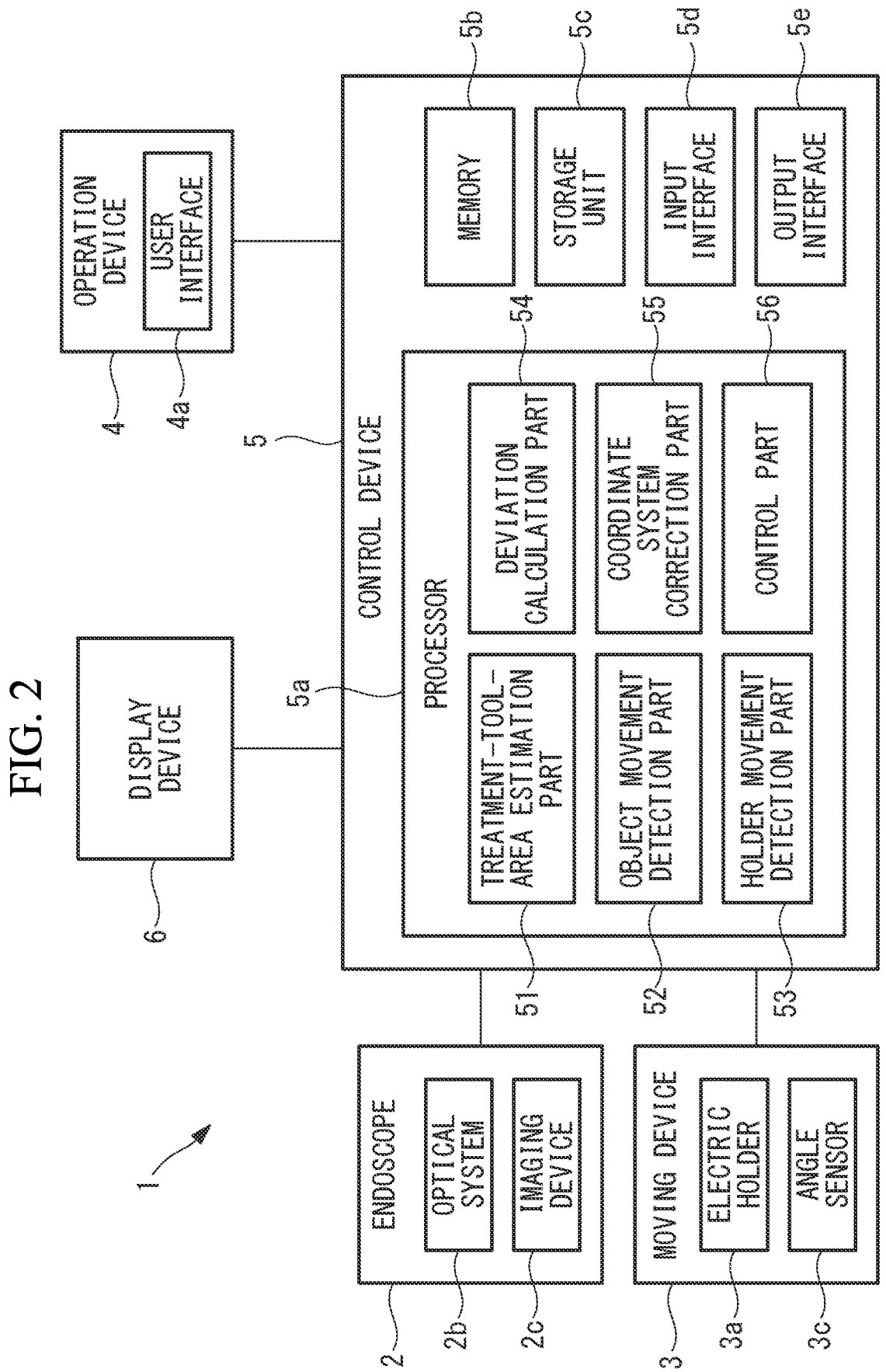
FIG. 2 is a block diagram showing the overall configuration of the endoscope system in FIG. 1.

As shown in FIGS. 1 and 2, an endoscope system 1 according to this embodiment includes an endoscope 2, a moving device 3 that holds and moves the endoscope 2, an operation device 4 operated by a user, a control device 5 that controls the moving device 3 according to operation signals from the operation device 4, and a display device 6.

The endoscope 2 is a rigid endoscope including a long, rigid lens barrel 2a, an optical system 2b that is disposed in the lens barrel 2a and collects light from an object, and an imaging device 2c that is fixed to the lens barrel 2a and captures an image of the collected light. The endoscope 2 is a forward-viewing endoscope having a visual axis (optical axis) B coaxial with a longitudinal axis A of the lens barrel 2a. The imaging device 2c is an image sensor, such as a charge-coupled device (CCD) image sensor or a complementary metal-oxide-semiconductor (CMOS) image sensor.

The endoscope 2 is inserted into the body together with at least one treatment tool 7, acquires an endoscopic image C (see FIGS. 3A to 3C) including the at least one treatment tool 7 with the imaging device 2c, and transmits the endoscopic image C to the display device 6. The display device 6 is any type of display, such as a liquid crystal display or an organic EL display. The operator operates the treatment tool 7 while observing the endoscopic image C displayed on the display device 6.

The moving device 3 includes an electric holder 3a that three-dimensionally controls the position and orientation of the endoscope 2. The electric holder 3a is a robot arm having multiple joints 3b. The proximal end of the endoscope 2 is held at the tip of the electric holder 3a so as to be rotatable about the longitudinal axis A. The tip of the electric holder 3a and the endoscope 2 are integrally moved by the action of the multiple joints 3b, and the position and orientation of the endoscope 2 are three-dimensionally changed. The moving device 3 includes angle sensors 3c for detecting the rotation angles of the respective joints 3b. The angle sensors 3c are, for example, encoders, potentiometers, or Hall sensors provided at the respective joints 3b.

The operation device 4 includes a user interface 4a including input devices, such as keys, a joystick, buttons, and a touch panel. The operator can input an instruction for moving the endoscope 2 to the operation device 4 by operating the user interface 4a. The operation device 4 transmits an operation signal based on the operation of the user interface 4a to the control device 5.

The user interface 4a can receive input of a trigger from the user. As will be described below, the trigger causes processing for correcting a holder coordinate system $\Sigma r$ to be performed.

As shown in FIG. 2, the control device 5 includes at least one processor 5a, a memory 5b, a storage unit 5c, an input interface 5d, and an output interface 5e.

The control device 5 is connected to other peripheral devices 2, 3, 4, and 6 via the input interface 5d and the output interface 5e, and transmits and receives an endoscopic image C, information about the rotation angles of the joints 3b, signals, and the like via the interfaces 5d and 5e.

The memory 5b is, for example, a semiconductor memory including a read-only memory (ROM) or random-access memory (RAM) area.

The storage unit 5c is a non-transitory computer-readable storage medium, and examples thereof include a nonvolatile storage medium including a hard disk and a semiconductor memory, such as a flash memory.

The processor 5a controls the moving device 3 according to the operation signal from the operation device 4 to move the endoscope 2 in accordance with an instruction input to the user interface 4a by the operator.

Figure 3A:
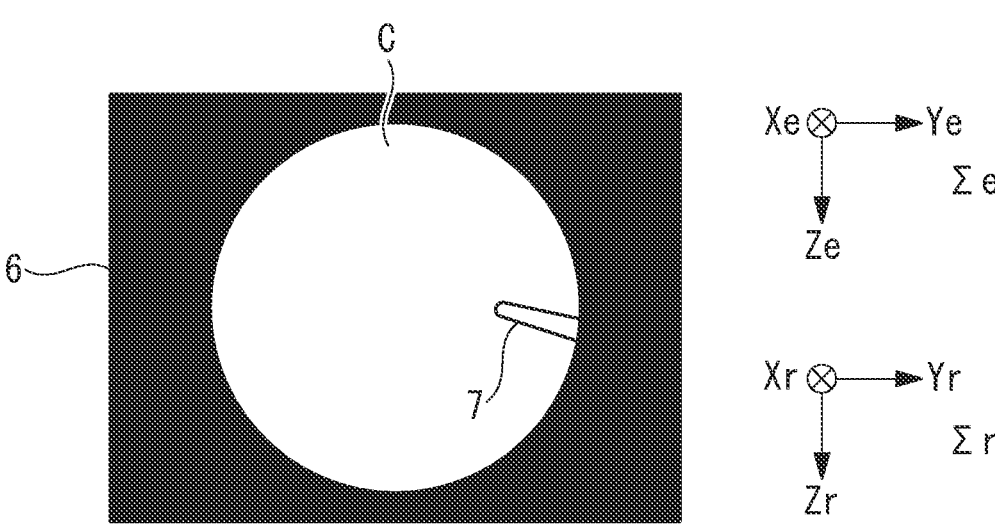
FIG. 3A illustrates an example endoscopic image displayed on a display device, illustrating the relationship between an endoscope coordinate system and a holder coordinate system.

Now, as shown in FIG. 3A, the holder coordinate system $\Sigma r$ is initially set such that the holder coordinate system $\Sigma r$ and an endoscope coordinate system $\Sigma e$ coincide with each other.

The endoscope coordinate system $\Sigma e$ is a coordinate system fixed to the lens barrel 2a and the imaging device 2c, and the holder coordinate system $\Sigma r$ is a coordinate system fixed to the tip of the electric holder 3a.

In one example, the endoscope coordinate system $\Sigma e$ is a Cartesian coordinate system having the Xe-axis, the Ye-axis, and the Ze-axis orthogonal to one another, and the holder coordinate system $\Sigma r$ is a Cartesian coordinate system having the Xr-axis, the Yr-axis, and the Zr-axis orthogonal to one another. The Xe-axis and the Xr-axis coincide with the longitudinal axis A, the Ye-axis and the Yr-axis are parallel to the horizontal direction (right-left direction) of the endoscopic image C, and the Ze-axis and the Zr-axis are parallel to the vertical direction (up-down direction) of the endoscopic image C. What is meant by that the holder coordinate system $\Sigma r$ and the endoscope coordinate system Ce coincide with each other is that the directions of the Xe-axis and the Xr-axis coincide with each other, the directions of the Ye-axis and the Yr-axis coincide with each other, and the directions of the Ze-axis and the Zr-axis coincide with each other.

Figure 3B:
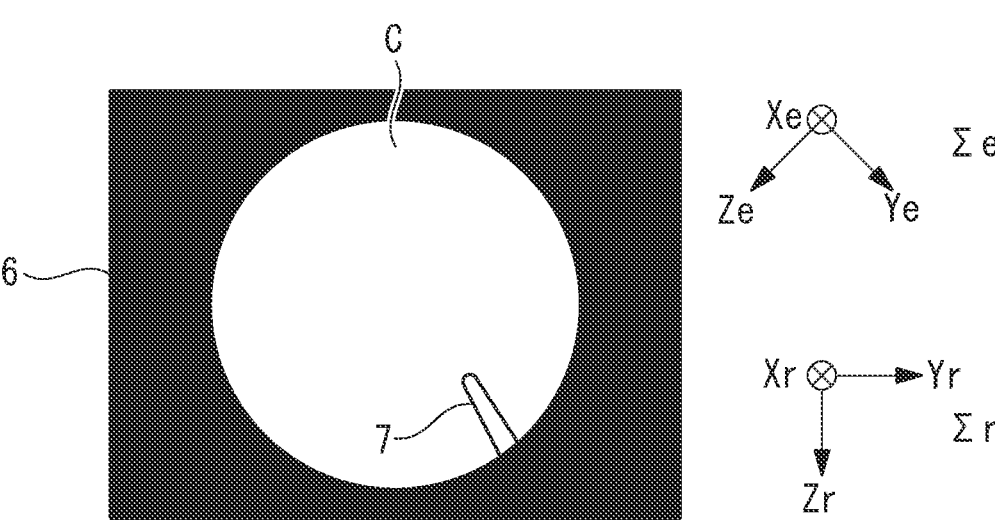
FIG. 3B illustrates an example endoscopic image displayed on the display device, illustrating the relationship between the endoscope coordinate system that has been rotated and the holder coordinate system.
Figure 3C:
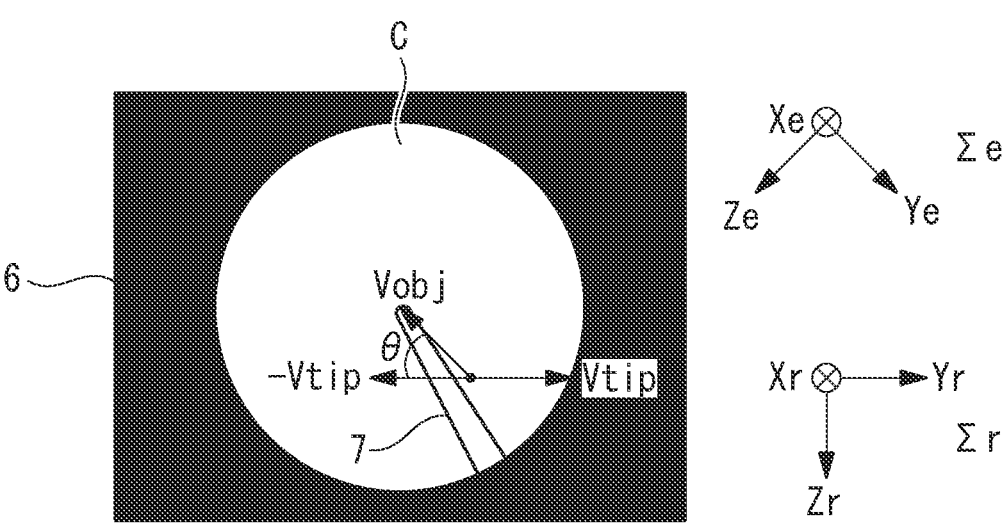
FIG. 3C illustrates an example endoscopic image displayed on the display device after the endoscope has been moved, illustrating the relationship between the endoscope coordinate system that has been rotated and the holder coordinate system.

However, as shown in FIG. 3B, when the endoscope 2 is rotated about the longitudinal axis A with respect to the moving device 3, the endoscope coordinate system de and the holder coordinate system $\Sigma r$ deviate from each other. Specifically, the endoscope coordinate system $\Sigma e$ rotates about the Xe-axis, which corresponds to the longitudinal axis A, and the endoscope coordinate system $\Sigma e$ deviates from the holder coordinate system $\Sigma r$ by a rotation angle $\theta$ of the endoscope 2 in the rotational direction about the Xe-axis.

When, as in this case, the endoscope coordinate system $\Sigma e$ does not coincide with the holder coordinate system $\Sigma r$, it is difficult for a user who is observing the endoscopic image C displayed on the display device 6 to intuitively and accurately move the endoscope 2 in a desired direction by operating the user interface 4a.

For example, if, in the case where the endoscope coordinate system $\Sigma e$ has been rotated by 90° with respect to the holder coordinate system $\Sigma r$, the user inputs an instruction for moving the endoscope 2 upward in the endoscopic image C to the user interface 4*a*, the moving device 3 moves the endoscope 2 leftward in the endoscopic image C.

The processor 5*a* can perform processing for correcting the holder coordinate system Σr on the basis of the deviation between the coordinate systems Σe and Σr.

Specifically, as shown in FIG. 2, the processor 5*a* includes: a treatment-tool-area estimation part (moving-body-area estimation part) 51 that estimates a treatment tool area (moving body area) D in an endoscopic image C; an object movement detection part 52 that detects the movement direction of an object S in the endoscopic image C; a holder movement detection part 53 that detects the movement direction of the tip of the electric holder 3*a*; a deviation calculation part 54 that calculates the deviation between the coordinate systems Σe and Σr on the basis of the movement direction of the object S and the movement direction of the tip of the electric holder 3*a*; a coordinate system correction part 55 that corrects the holder coordinate system Σr on the basis of the estimated deviation; and a control part 56 that controls the moving device 3 on the basis of the holder coordinate system Σr.

The processor 5*a* realizes the functions of the parts 51, 52, 53, 54, 55, and 56, described below, by performing processing in accordance with a coordinate system correction program (not shown) stored in the storage unit 5*c* and read out into the memory 5*b*.

Figure 4A:
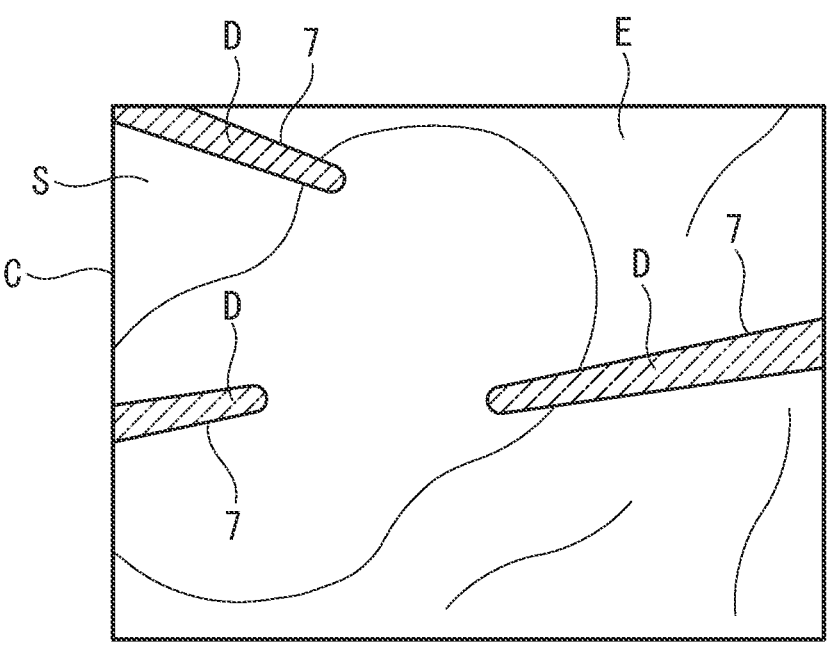
FIG. 4A illustrates an example of treatment tool areas and another area in an endoscopic image.

As shown in FIG. 4A, the treatment-tool-area estimation part 51 recognizes treatment tools (moving bodies) 7 in an endoscopic image C using a known method, such as image recognition utilizing artificial intelligence, and estimates the areas of the treatment tools 7 as treatment tool areas D. The object movement detection part 52 detects the movement direction of the object S on the basis of another area E excluding the treatment tool areas D in the endoscopic image C. Specifically, the object movement detection part 52 estimates a motion vector Vobj of the object S in the other area E from at least two endoscopic images C captured at different times, using a known method such as optical flow or visual simultaneous localization and mapping (SLAM). The motion vector Vobj is a two-dimensional vector representing the movement direction of the object S in the YeZe plane orthogonal to the Xe-axis, and represents the movement direction of the endoscope 2 in the endoscope coordinate system Σe. Specifically, the motion vector Vobj and the movement direction of the endoscope 2 are opposite to each other.

The holder movement detection part 53 acquires, from the moving device 3, the rotation angles of the joints 3*b* detected by the angle sensors 3*c*, calculates the position of the tip of the electric holder 3*a* from the rotation angles of the joints 3*b*, and calculates the velocity Vtip of the tip of the electric holder 3*a* from the change in the position with time. The velocity Vtip is a two-dimensional vector representing the movement direction of the tip of the electric holder 3*a* in the YrZr plane orthogonal to the Xr-axis, and represents the movement direction of the endoscope 2 in the holder coordinate system Σr.

The deviation calculation part 54 calculates a deviation θ between the coordinate systems Σe and Σr from Equation (1) below using the motion vector Vobj and the velocity Vtip. The deviation e corresponds to the rotation angle θ of the endoscope 2 about the longitudinal axis A with respect to the electric holder 3*a*.

$$\theta = \cos^{-1}\left(\frac{-Vtip \cdot Vobj}{|Vtip| \cdot |Vobj|}\right) \tag{1}$$

The coordinate system correction part 55 corrects the holder coordinate system Σr on the basis of the deviation e to make the holder coordinate system Σr coincide with the endoscope coordinate system Σe. Specifically, the coordinate system correction part 55 corrects the Denavit-Hartenberg (DH) parameters of the electric holder 3*a* on the basis of the deviation θ, so that the holder coordinate system Σr coincides with the endoscope coordinate system Ce.

The control part 56 controls the moving device 3 on the basis of the corrected holder coordinate system Σr.

Figure 5:
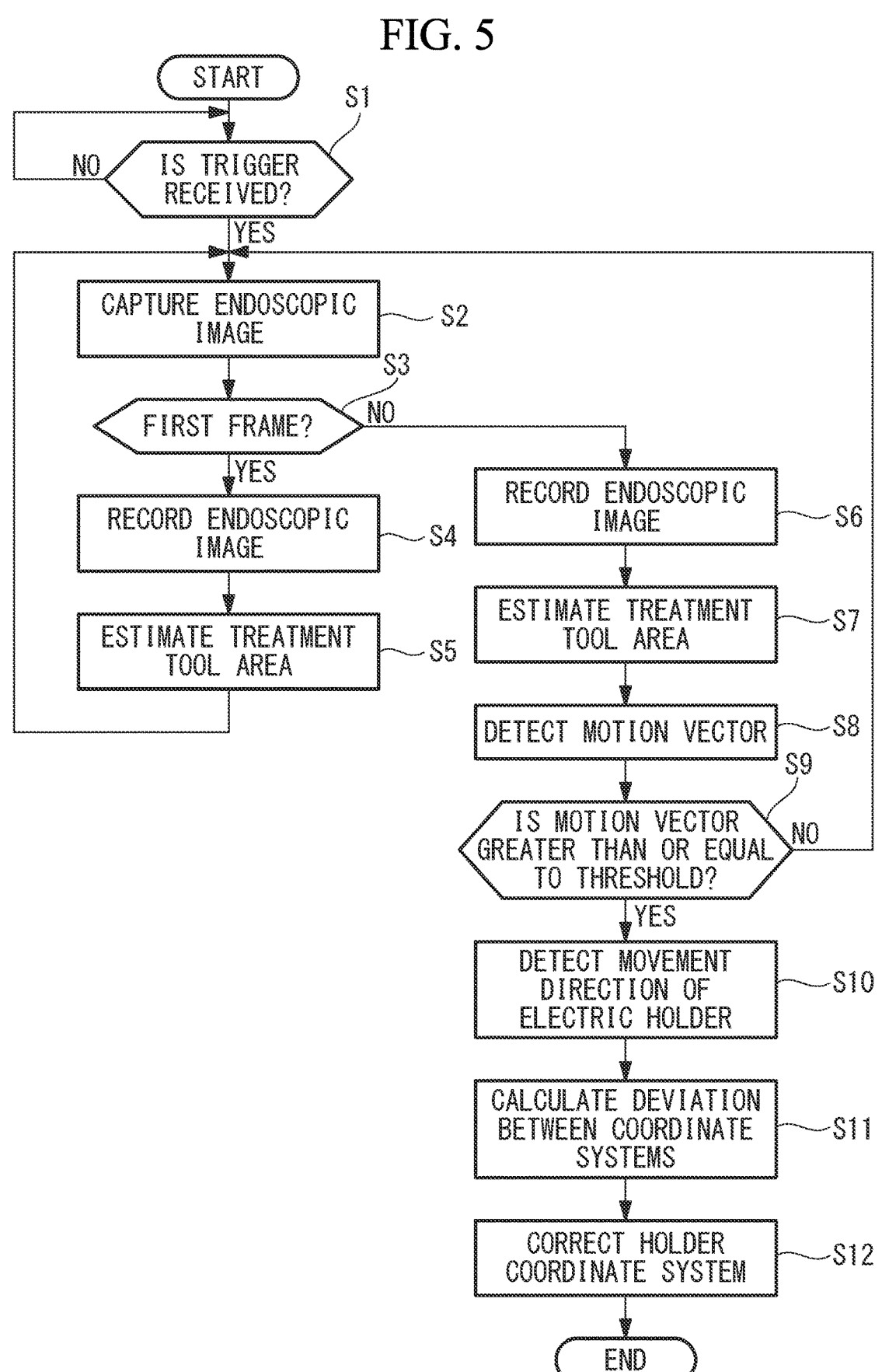
FIG. 5 is a flowchart of a coordinate system correction method according to the first embodiment of the present invention.

Next, a coordinate system correction method performed by the processor 5*a* will be described with reference to FIG. 5.

A user inputs a trigger to the user interface 4*a* at a desired time when the user wishes to correct the holder coordinate system Σr. For example, the user manually rotates the endoscope 2 about the longitudinal axis A with respect to the electric holder 3*a* in order to adjust the orientation of the object S in the endoscopic image C displayed on the display device 6, and then inputs the trigger to the user interface 4*a*.

Subsequently, the user operates the operation device 4 to move the tip of the electric holder 3*a* and the endoscope 2.

In response to the user interface 4*a* receiving the trigger (YES in step S1), the processor 5*a* performs processing for correcting the holder coordinate system Σr (steps S2 to S12).

Specifically, while the tip of the electric holder 3*a* and the endoscope 2 are moved, the processor 5*a* acquires an endoscopic image C at a predetermined time interval (step S2), and records the acquired endoscopic images C in the memory 5*b*or the storage unit 5*c* (steps S4 and S6).

The endoscopic image C at the time when the trigger is received is first acquired and stored as a first frame (YES in step S3, and step S4), and the treatment tool areas D in the first frame of the endoscopic image C are estimated by the treatment-tool-area estimation part 51 (step S5).

Thereafter, every time a new endoscopic image C is acquired (step S2), the newly acquired endoscopic image (i.e., the current endoscopic image) C is stored (step S6), the treatment-tool-area estimation part 51 estimates the treatment tool areas D in the current endoscopic image C (step S7), and the object movement detection part 52 detects the motion vector Vobj using the current endoscopic image C and the previously acquired first frame of the endoscopic image C (step S8). In step S8, the treatment tool areas D are excluded from the two endoscopic images C, namely, the current endoscopic image C and the first frame of the endoscopic image C, and the motion vector Vobj is estimated on the basis of only the other areas E in the two endoscopic images C.

If the magnitude of the motion vector Vobj is greater than or equal to a threshold (YES in step S9), the holder movement detection part 53 detects the velocity Vtip of the tip of the electric holder 3*a* from the change in the position of the tip of the electric holder 3*a* with time from the time when the first frame of the endoscopic image C is captured to the time when the current endoscopic image C is captured (step S10).

Next, the deviation calculation part 54 calculates the deviation θ between the coordinate systems Σe and Σr from the velocity Vtip and the motion vector Vobj (step S11).

Next, the coordinate system correction part 55 corrects the holder coordinate system Σr on the basis of the deviation θ to make the holder coordinate system Σr coincide with the endoscope coordinate system Σe (step S12).

If the magnitude of the motion vector Vobj is less than the threshold (NO in step S9), the process returns to step S2 without going through steps S10 to S12, and steps S2, S6, S7, and S8 are repeated until the magnitude of the motion vector Vobj reaches or exceeds the threshold.

After step S12, the moving device 3 is controlled by the control part 56 on the basis of the corrected holder coordinate system Σr, in accordance with the instruction input to the user interface 4a.

An endoscopic image C can include a moving object (moving body) in addition to a stationary object S. The moving object influences the accuracy of the motion vector Vobj, so, it is difficult to estimate the motion vector of the object accurately representing the movement direction of the endoscope 2 from the endoscopic image C including the moving object. In particular, the treatment tools 7 move in the endoscopic image C during surgery.

According to this embodiment, the other area E excluding the treatment tool areas D in the endoscopic image C is used to estimate the motion vector Vobj. Thus, even when there are moving treatment tools 7 in the endoscopic image C, an accurate motion vector Vobj accurately representing the movement direction of the endoscope 2 can be estimated. By calculating the accurate deviation θ between the coordinate systems Σe and Σr on the basis of the accurate motion vector Vobj, the holder coordinate system Σr can be accurately corrected. Furthermore, the endoscope 2 can be moved by the moving device 3 in a direction accurately corresponding to the direction input to the operation device 4 by the user, on the basis of the accurately corrected holder coordinate system Σr.

Furthermore, the deviation θ between the coordinate systems Σe and Σr is calculated only from at least two endoscopic images C and the information about the position of the tip of the electric holder 3a. In other words, there is no need to add a device, such as a sensor, for detecting the deviation θ; that is, the deviation θ can be estimated without a sensor. Accordingly, modification of the electric holder 3a is unnecessary, and the diameter and size of the electric holder 3a can be easily reduced.

By adding a device, such as a sensor, for detecting the rotation angle θ of the endoscope 2 to the electric holder 3a, measurement of the deviation θ can be easily achieved. However, in that case, the conventional electric holder cannot be used, and the electric holder needs to be modified. Furthermore, the outer diameter, size, and weight of the electric holder increase, and the electric holder 3a may hinder the surgery.

Figure 4B:
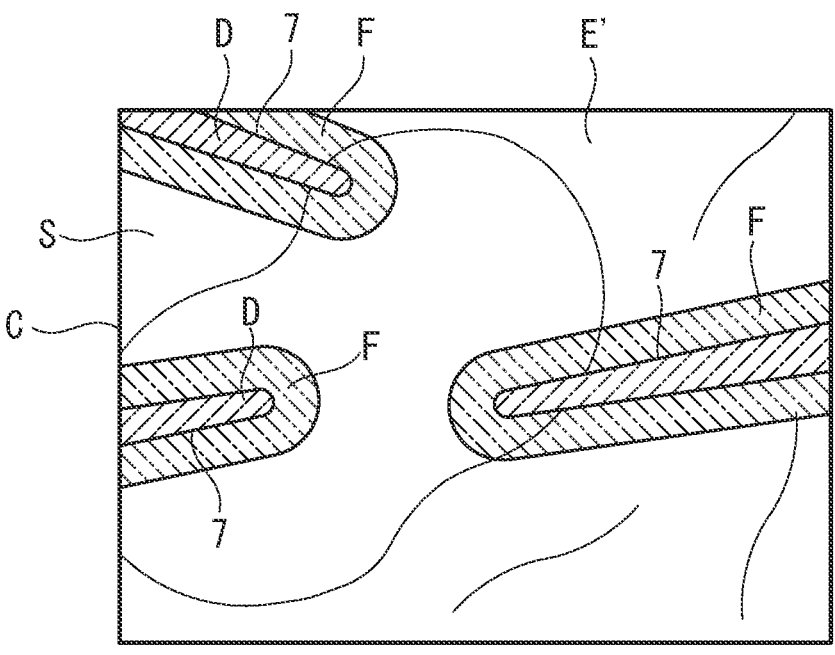
FIG. 4B illustrates an example of the treatment tool areas, margins, and the other area in the endoscopic image.

In this embodiment, as shown in FIG. 4B, the treatment-tool-area estimation part 51 may estimate the movement direction of the object S on the basis of another area E' excluding the areas obtained by adding margins F to the treatment tool areas D.

The margins F are areas extending along the contours of the treatment tool areas D and surrounding the treatment tool areas D, and are, for example, band-shaped areas having a predetermined width.

In the vicinity of the treatment tools 7, the movement of the object S may be influenced by the movements of the treatment tools 7. For example, when the object S is pushed or pulled by the treatment tools 7, the object S may partially move in the vicinity of the treatment tools 7.

By excluding the areas obtained by adding the margins F to the treatment tool areas D, it is possible to improve the estimation accuracy of the motion vector Vobj of the object S and to more accurately estimate the deviation θ between the coordinate systems Σe and Σr.

Second Embodiment

Next, an endoscope system and a coordinate system correction method according to a second embodiment of the present invention will be described.

This embodiment differs from the first embodiment in that an endoscope 21 is an oblique-viewing endoscope. In this embodiment, the configurations different from those in the first embodiment will be described. The same configurations as those in the first embodiment will be denoted by the same reference numerals, and the description thereof will be omitted.

The endoscope system according to this embodiment includes the endoscope 21, the moving device 3, the operation device 4, the control device 5, and the display device 6.

Figure 6:
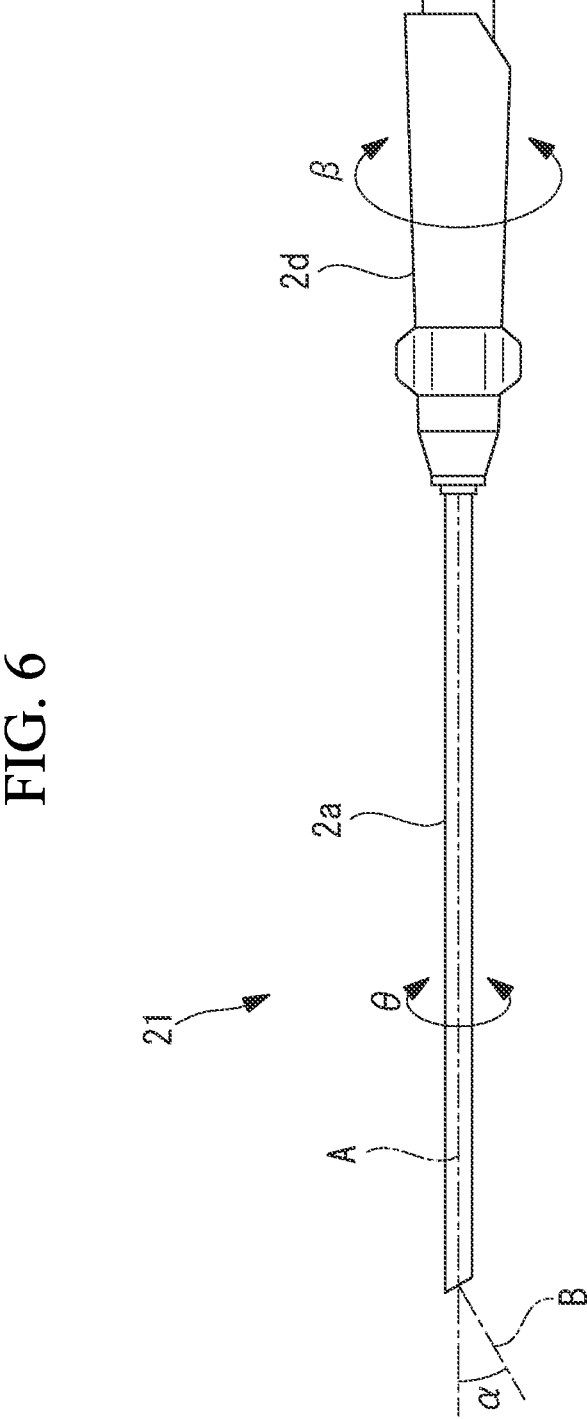
FIG. 6 illustrates an oblique-viewing endoscope in an endoscope system according to a second embodiment of the present invention.

As shown in FIG. 6, the endoscope 21 is an oblique-viewing rigid endoscope having a visual axis B inclined with respect to the longitudinal axis A. The endoscope 21 includes the long, rigid lens barrel 2a, and an operation part 2d connected to the proximal end of the lens barrel 2a. The operation part 2d is rotatable about the longitudinal axis A with respect to the lens barrel 2a, and the imaging device 2c is held inside the operation part 2d and fixed to the operation part 2d. The electric holder 3a holds the lens barrel 2a so as to allow rotation about the longitudinal axis A. The imaging device 2c is a three-dimensional camera and can acquire a stereo image including three-dimensional position information of the object S as an endoscopic image C.

When the lens barrel 2a and the operation part 2d integrally rotate with respect to the electric holder 3a, the visual axis B rotationally moves about the longitudinal axis A, changing the direction of the visual axis B. Furthermore, when the operation part 2d rotates with respect to the lens barrel 2a and the electric holder 3a, the imaging device 2c rotates about the longitudinal axis A, rotating the endoscopic image C displayed on the display device 6.

As described, in this embodiment, when the lens barrel 2a rotates with respect to the electric holder 3a, and when the operation part 2d rotates with respect to the lens barrel 2a, the endoscope coordinate system Σe rotates with respect to the holder coordinate system Σr. Hence, the deviation between the endoscope coordinate system Σe and the holder coordinate system Σr is calculated from the rotation angle θ of the lens barrel 2a about the longitudinal axis A and the rotation angle β of the operation part 2d about the longitudinal axis A.

Figure 7:
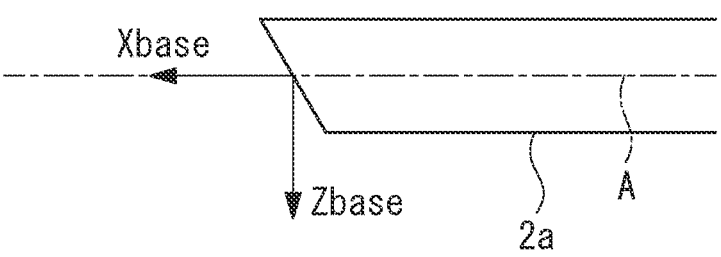
FIG. 7 illustrates a method for calculating an endoscope coordinate system of the oblique-viewing endoscope.
Figure 7:
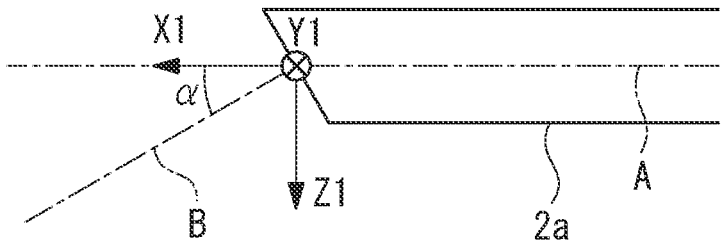
Figure 7:
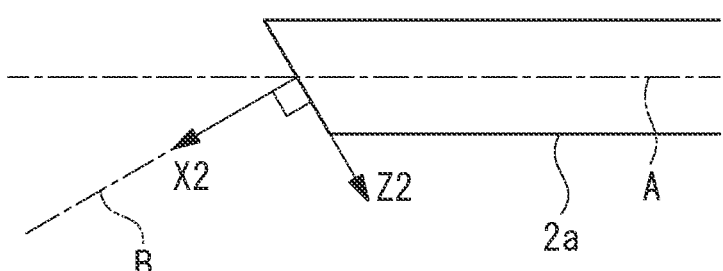
Figure 7:
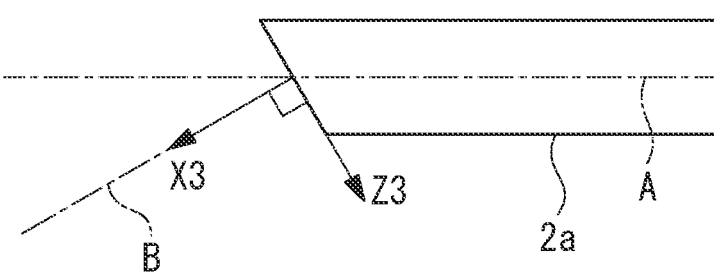

FIG. 7 illustrates a method for calculating the rotation angle θ of the lens barrel 2a and the rotation angle β of the operation part 2d.

An XbaseYbaseZbase reference coordinate system is set at the tip of the endoscope 21. The Xbase axis coincides with the longitudinal axis A. A coordinate system obtained by rotating the XbaseYbaseZbase reference coordinate system by θ about the Xbase axis is assumed to be an X1Y1Z1 coordinate system. The rotation about the Xbase axis corresponds to the rotation of the lens barrel 2a. A coordinate system obtained by rotating the X1Y1Z1 coordinate system about the Y1 axis by an inclination angle α (for example, −30 deg) of the visual axis B is assumed to be an X2Y2Z2 coordinate system. A coordinate system obtained by rotating the X2Y2Z2 coordinate system by β about the X2 axis is assumed to be an X3Y3Z3 coordinate system. The rotation about the X2 axis corresponds to the rotation of the operation part 2d. The X3Y3Z3 coordinate system is the endoscope coordinate system Σe after the lens barrel 2a and the operation part 2d have been rotated.

From the definitions above, the following equation is established.

$$H^1_{base}(0) \cdot H^1_2(\alpha) \cdot H^3_2(0) \cdot \begin{bmatrix} vx \\ vy \\ vz \\ 1 \end{bmatrix} = H^1_{base}(\theta) \cdot H^1_2(\alpha) \cdot H^3_2(\beta) \cdot \begin{bmatrix} vx' \\ vy' \\ pz' \\ 1 \end{bmatrix}$$

$$\begin{bmatrix} C\alpha & 0 & S\alpha & 0 \\ 0 & 1 & 0 & 0 \\ -S\alpha & 0 & C\alpha & 0 \\ 0 & 0 & 0 & 1 \end{bmatrix} \cdot \begin{bmatrix} vx \\ vy \\ vz \\ 1 \end{bmatrix} = \begin{bmatrix} 1 & 0 & 0 & 0 \\ 0 & C\theta & -S\theta & 0 \\ 0 & S\theta & C\theta & 0 \\ 0 & 0 & 0 & 1 \end{bmatrix} \cdot$$

$$\begin{bmatrix} C\alpha & 0 & S\alpha & 0 \\ 0 & 1 & 0 & 0 \\ -S\alpha & 0 & C\alpha & 0 \\ 0 & 0 & 0 & 1 \end{bmatrix} \begin{bmatrix} 1 & 0 & 0 & 0 \\ 0 & C\beta & -S\beta & 0 \\ 0 & S\beta & C\beta & 0 \\ 0 & 0 & 0 & 1 \end{bmatrix} \cdot \begin{bmatrix} vx' \\ vy' \\ vz' \\ 1 \end{bmatrix}$$

$$\begin{bmatrix} vx' \\ vy' \\ vz' \\ 1 \end{bmatrix} = \begin{bmatrix} 1 & 0 & 0 & 0 \\ 0 & C\beta & -S\beta & 0 \\ 0 & S\beta & C\beta & 0 \\ 0 & 0 & 0 & 1 \end{bmatrix}^{-1} \cdot$$

$$\begin{bmatrix} vx' \\ vy' \\ vz' \\ 1 \end{bmatrix} = \begin{bmatrix} C\alpha & 0 & S\alpha & 0 \\ 0 & 1 & 0 & 0 \\ -S\alpha & 0 & C\alpha & 0 \\ 0 & 0 & 0 & 1 \end{bmatrix}^{-1} \begin{bmatrix} 1 & 0 & 0 & 0 \\ 0 & C\theta & -S\theta & 0 \\ 0 & S\theta & C\theta & 0 \\ 0 & 0 & 0 & 1 \end{bmatrix}^{-1} \cdot \begin{bmatrix} C\alpha & 0 & S\alpha & 0 \\ 0 & 1 & 0 & 0 \\ -S\alpha & 0 & C\alpha & 0 \\ 0 & 0 & 0 & 1 \end{bmatrix} \begin{bmatrix} vx \\ vy \\ vz \\ 1 \end{bmatrix}$$

$$\begin{bmatrix} vx' \\ vy' \\ vz' \\ 1 \end{bmatrix} = \begin{bmatrix} (C\alpha^2 + S\alpha^2 C\theta)vx + S\alpha S\theta py + (S\alpha C\alpha - S\alpha C\alpha C\theta)vz \\ (-S\alpha S\theta vx + C\theta vy + C\alpha S\theta vz) \cdot C\beta - \\ \{(S\alpha C\alpha - S\alpha C\alpha C\theta)vx - C\alpha S\theta py + (S\alpha^2 + C\alpha^2 C\theta)vz\} \cdot S\beta \\ (-S\alpha S\theta vx + C\theta vy + C\alpha S\theta vz) \cdot S\beta + \{(S\alpha C\alpha - S\alpha C\alpha C\theta)vx - \\ C\alpha S\theta vy + (S\alpha^2 + C\alpha^2 C\theta)vz\} \cdot C\beta \\ 1 \end{bmatrix}$$

where $V=(vx, vy, vz)^T$ is the three-dimensional velocity of the endoscope 21 in the holder coordinate system Σr, and is the velocity Vtip of the tip of the electric holder 3a detected by the holder movement detection part 53; $V'=(vx', vy', vz')^T$ is the calculated velocity of the endoscope 21 in the endoscope coordinate system Σe calculated from the rotation angles θ and β and the velocity V; and $H^i_{i-1}$ is a homogeneous transformation matrix from an i−1 coordinate system to an i coordinate system. In addition, Cθ=cos θ, and Sθ=sin θ.

Assuming that the velocity of the endoscope 21 in the endoscope coordinate system Σe calculated from the endoscopic image C is V", the rotation angle θ of the lens barrel 2a and the rotation angle β of the operation part 2d can be estimated by calculating the rotation angles θ and β with which the difference between V' and V" is minimum, as shown in Equation (2) below.

$$(\theta, \beta) = \operatorname{argmin}(|vx' - vx''| + |vy' - vy''| + |vz' - vz''|) \qquad (2)$$

The velocity V" is a motion velocity Vobj of the object S detected by the object movement detection part 52. In step S8, the object movement detection part 52 acquires three-dimensional position information of the object S from each of multiple endoscopic images C, estimates the position and orientation of the endoscope 21 from the multiple endoscopic images C using a known image processing technique such as Structure from Motion (SfM) or Visual SLAM, and calculates the velocity V"=Vobj of the endoscope 21 in the endoscope coordinate system Σe from the amount of change of the estimated position and orientation.

In step S11, the deviation calculation part 54 calculates, as the deviation, the rotation angles θ and β with which the difference between V' and V" is minimum, by comprehensively changing the rotation angles θ and β.

In step S12, the coordinate system correction part 55 corrects the holder coordinate system Σr on the basis of the rotation angles θ and βv to make the holder coordinate system Σr coincide with the endoscope coordinate system Σe. Specifically, the coordinate system correction part 55 corrects the DH parameters of the electric holder 3a on the basis of the rotation angles θ and β, so that the holder coordinate system Σr coincides with the endoscope coordinate system Σe.

In this case, also in step S8 of this embodiment, the other area E excluding the treatment tool areas D in the endoscopic image C is used to estimate the motion vector Vobj. Therefore, even when there are moving treatment tools 7 in the endoscopic image C, an accurate motion vector Vobj accurately representing the movement direction of the oblique-viewing endoscope 21 can be estimated. By calculating the accurate deviations θ and β between the coordinate systems Σe and Σr on the basis of the accurate motion vector Vobj, the holder coordinate system Σr can be accurately corrected.

Other advantages and effects in this embodiment are the same as those in the first embodiment, so, the description thereof will be omitted.

Also in this embodiment, similarly to the first embodiment, the movement direction Vobj of the object S may be estimated on the basis of the other area E' excluding the areas obtained by adding the margins F to the treatment tool areas D.

Third Embodiment

Next, an endoscope system and a coordinate system correction method according to a third embodiment of the present invention will be described.

This embodiment differs from the first embodiment in the method for detecting the movement direction of the object S. In this embodiment, the configurations different from those in the first embodiment will be described. The same configurations as those in the first embodiment will be denoted by the same reference numerals, and the description thereof will be omitted.

Similarly to the first embodiment, the endoscope system 1 according to this embodiment includes the endoscope 2, the moving device 3, the operation device 4, the control device 5, and the display device 6.

Figures 8, 9:
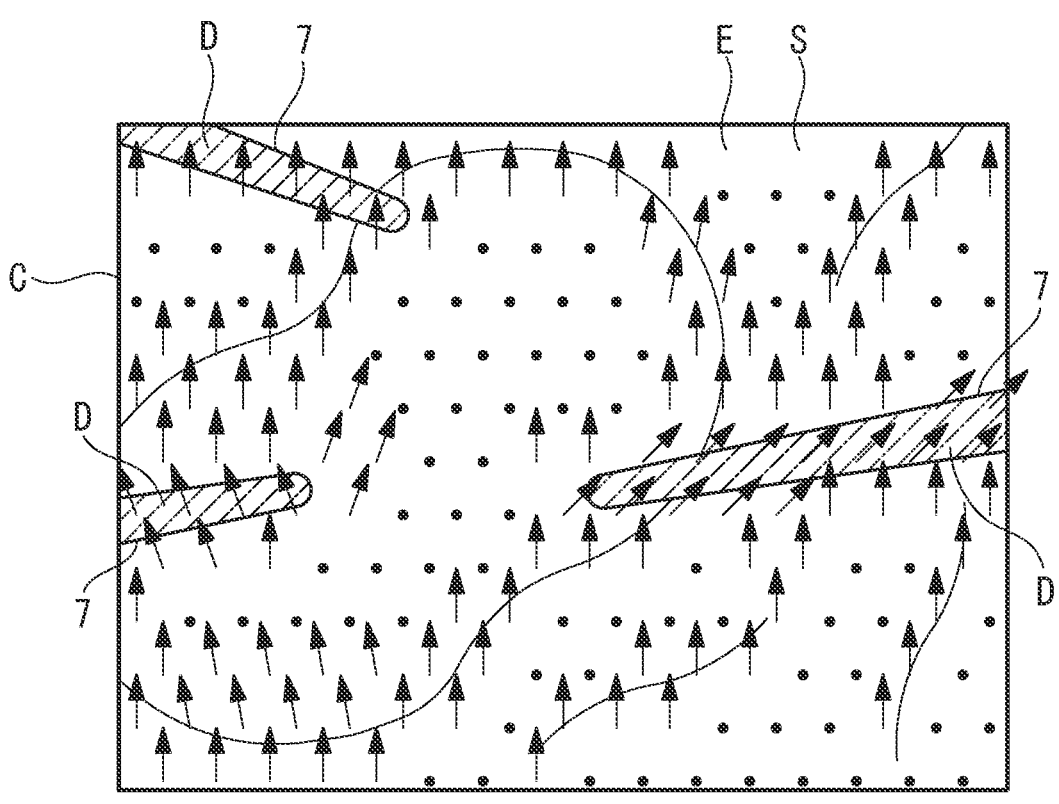
FIG. 8 illustrates a method for estimating a motion vector of an object with an endoscope system according to a third embodiment of the present invention, illustrating motion vectors at the respective positions in an endoscopic image.
FIG. 9 illustrates a method for estimating a motion vector of an object with an endoscope system according to a fourth embodiment of the present invention, and is a table showing the direction and the number of motion vectors.

As shown in FIG. 8, in step S8, the object movement detection part 52 estimates motion vectors u (see arrows) at the respective positions in the endoscopic image C, selects the motion vectors u at the positions in the other area E excluding the treatment tool areas D, and estimates the motion vector Vobj of the object S from the selected motion vectors u. For example, the motion vector Vobj is the average of the selected motion vectors u.

Black dots in the endoscopic image C of FIG. 8 represent the positions where the motion vectors u are not estimated due to the lack or absence of features (change in gradation value) such as edges. The positions where the motion vectors are not estimated may also be excluded when the motion vector Vobj of the object S is estimated.

In an actual surgical scene, the object S, such as an organ in the other area E, is not necessarily completely stationary.

For example, the object S in the other area E may partially move when pushed or pulled by the treatment tools 7. Such a movement of the object S causes an estimation error of the motion vector Vobj.

According to this embodiment, the estimation error of the motion vector Vobj of the object S can be reduced by using the motion vectors u at multiple positions in the other area E.

Other advantages and effects in this embodiment are the same as those in the first embodiment, so the description thereof will be omitted.

Also in this embodiment, similarly to the first embodiment, the movement direction Vobj of the object S may be estimated on the basis of the other area E' excluding the areas obtained by adding the margins F to the treatment tool areas D. Specifically, the object movement detection part 52 may select the motion vectors u at positions in the other area E' and estimate the motion vector Vobj of the object S from the selected motion vectors u.

Fourth Embodiment

Next, an endoscope system and a coordinate system correction method according to a fourth embodiment of the present invention will be described.

This embodiment differs from the third embodiment in that only the motion vectors u selected according to the direction from the motion vectors u at positions in the other area E are used to estimate the motion vector Vobj of the object S. In this embodiment, the configurations different from those in the first and third embodiments will be described. The same configurations as those in the first and third embodiments will be denoted by the same reference numerals, and the description thereof will be omitted.

In step S8 of this embodiment, as shown in FIG. 9, the object movement detection part 52 selects motion vectors u at positions in the other area E, and then additionally selects motion vectors u according to the direction di (i=1, 2, 3, . . .) of the motion vectors u.

Specifically, the object movement detection part 52 counts the number ni (i=1, 2, 3, . . . ) of motion vectors u for each direction di (=1, 2, 3, . . . ).

Next, the object movement detection part 52 selects the motion vectors u that are present in the largest number and the motion vectors whose direction is close to the direction of the motion vectors u that are present in the largest number. For example, the motion vectors u whose direction is within $\pm\delta°$ with respect to the motion vectors u that are present in the largest number are selected: δ is a value set as appropriate. In the example in FIG. 9, the number n3 of motion vectors u in the direction d3 is the largest. So, the motion vectors u in the direction d3 and the motion vectors in the directions d2 and d4 are selected.

Next, the object movement detection part 52 estimates the motion vector Vobj of the object S only from the selected motion vectors u.

As described above, the object S in the other area E may partially move regardless of the movement of the endoscope 2.

According to this embodiment, the motion vectors u in the directions d1, d5, and d6, which are different from the direction d3 in which the object S moves due to the movement of the endoscope 2, are excluded from the motion vectors u in the other area E, and only the motion vectors u in the direction d3, in which the object S moves due to the movement of the endoscope 2, and in the directions d2 and d4 close thereto are used to estimate the motion vector Vobj.

This further reduces the estimation error of the motion vector Vobj of the object S, as compared with the third embodiment.

Other advantages and effects in this embodiment are the same as those in the first embodiment, so, the description thereof will be omitted.

Also in this embodiment, similarly to the first embodiment, the movement direction Vobj of the object S may be estimated on the basis of the other area E' excluding the areas obtained by adding the margins F to the treatment tool areas D.

Fifth Embodiment

Next, an endoscope system and a coordinate system correction method according to a fifth embodiment of the present invention will be described.

This embodiment differs from the third and fourth embodiments in that enhancement processing is performed on the endoscopic image C used for the estimation of the motion vector Vobj. In this embodiment, the configurations different from those in the first, third, and fourth embodiments will be described. The same configurations as those in the first, third, and fourth embodiments will be denoted by the same reference numerals, and the description thereof will be omitted.

As described above, it is difficult to estimate the motion vectors u at positions where no or few features exist. The object movement detection part 52 performs enhancement processing, such as edge enhancement processing or contrast enhancement processing, for enhancing the features on the endoscopic image C. For example, the object movement detection part 52 divides the endoscopic image C into multiple N×M areas and performs the enhancement processing on each area such that the luminance histograms of the multiple areas are equal. If necessary, the object movement detection part 52 may perform preprocessing, such as grayscale conversion, on a color endoscopic image C before the enhancement processing.

Figure 10:
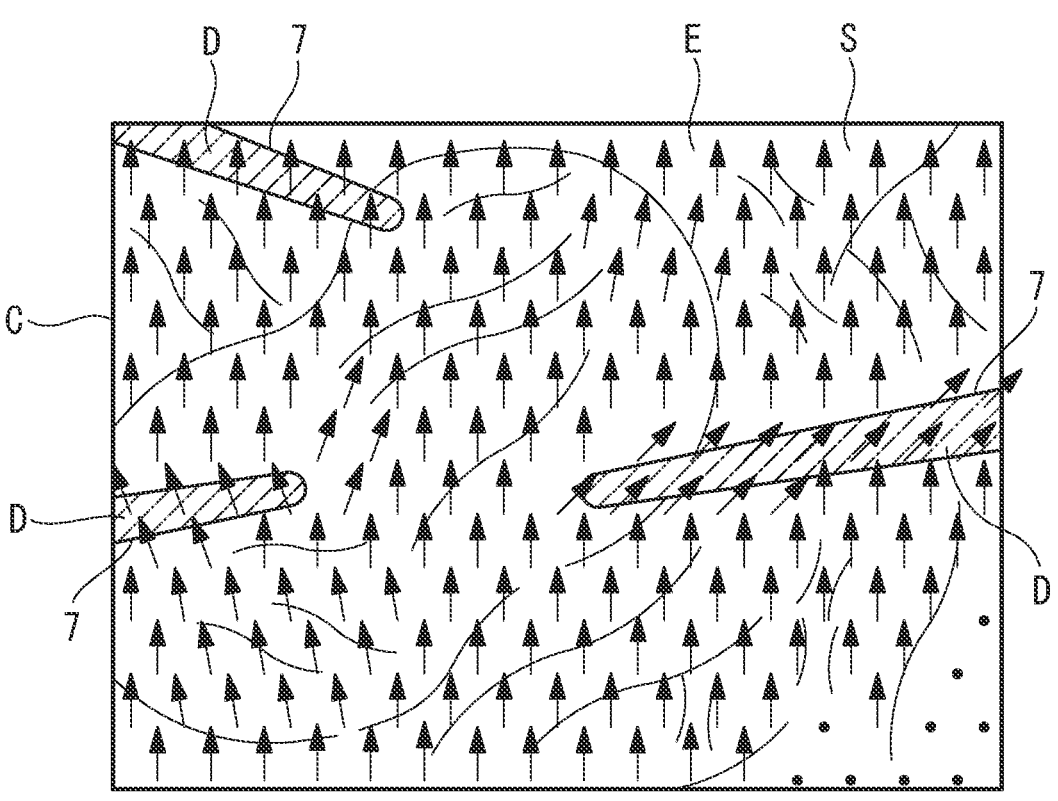
FIG. 10 illustrates a method for estimating a motion vector of an object with an endoscope system according to a fifth embodiment of the present invention, illustrating motion vectors at the respective positions in an endoscopic image that has gone through enhancement processing.

Next, the object movement detection part 52 estimates the motion vector Vobj using at least two endoscopic images C that have been subjected to the enhancement processing. FIG. 10 shows motion vectors u in an endoscopic image C that has been subjected to the enhancement processing. As shown in FIGS. 8 and 10, in the endoscopic image C that has been subjected to the enhancement processing, the motion vectors u are estimated also at positions where the motion vectors u are not estimated in the endoscopic image C that has not been subjected to the enhancement processing.

As described above, according to this embodiment, by performing processing for enhancing the features on the endoscopic image C, the area in which the motion vectors u are estimated increases, and the area that contributes to accurate estimation of the motion vector Vobj of the object S increases. This further reduces the estimation error of the motion vector Vobj of the object S, as compared with the third and fourth embodiments.

Other advantages and effects in this embodiment are the same as those in the first embodiment, so, the description thereof will be omitted.

Also in this embodiment, similarly to the first embodiment, the movement direction Vobj of the object S may be estimated on the basis of the other area E' excluding the areas obtained by adding the margins F to the treatment tool areas D.

Although it has been described in the first to fifth embodiments that the moving body is the treatment tool 7, the moving body is not limited to the treatment tool 7, and may be any object that moves in the endoscopic image C. For example, the moving body may be: a surgical instrument such as a trocar or a surgical tape; an organ such as the intestine, which performs peristalsis, or the diaphragm, which moves by breathing; or smoke generated when tissue is cauterized by a treatment tool or the like.

In the first to fifth embodiments, the treatment-tool-area estimation part 51 estimates the areas of the moving bodies such as the treatment tools 7 by means of image recognition using the artificial intelligence. Instead, the areas of the moving bodies may be estimated on the basis of motion vectors u at the respective positions in the endoscopic image C. For example, the treatment-tool-area estimation part 51 may estimate positions where the magnitudes of the motion vectors u are greater than or equal to a threshold as the areas of the moving bodies.

Also with this configuration, it is possible to estimate the areas of the moving treatment tools 7. If another moving body is included in the endoscopic image C instead of or in addition to the treatment tools 7, the area of the other moving body can also be estimated on the basis of the motion vectors u. Therefore, if there is another moving body in the endoscopic image C, it is possible to estimate an accurate motion vector Vobj accurately representing the movement direction of the endoscope 2 on the basis of the other area excluding the area of the other moving body.

In the first to fifth embodiments, the deviation between the coordinate systems $\Sigma e$ and $\Sigma r$ is caused by the rotation of the endoscope 2 or 21 about the longitudinal axis A with respect to the moving device 3. However, the present invention may also be applied to the case where the deviation between the coordinate systems $\Sigma e$ and $\Sigma r$ is caused by any relative movement between the endoscope 2 or 21 and the moving device 3. Specifically, it is possible to calculate the deviation between the coordinate systems $\Sigma e$ and $\Sigma r$ in a desired direction from the movement direction of the endoscope 2 moved by the electric holder 3 in the holder coordinate system $\Sigma r$ and the movement direction of the object S in the endoscopic image C. Therefore, at least one of the endoscope coordinate system $\Sigma e$ and the holder coordinate system $\Sigma r$ can be corrected on the basis of the calculated deviation, such that the endoscope coordinate system $\Sigma e$ and the holder coordinate system $\Sigma r$ coincide with each other.

REFERENCE SIGNS LIST

1 Endoscope system
2, 21 Endoscope
2*a* Lens barrel
2*c* Imaging device
2*d* Operation part
3 Moving device
3*a* Electric holder, robot arm
4 Operation device
4*a* User interface
5 Control device
5*a* Processor
7 Treatment tool (moving body)
A Longitudinal axis of endoscope
B Visual axis of endoscope
C Endoscopic image
D Treatment tool area (moving body area)
E, E' Other area
F Margin
S Object $\Sigma r$ Holder coordinate system (coordinate system of moving device)
$\Sigma e$ Endoscope coordinate system (coordinate system of endoscope)

The invention claimed is:

1. An endoscope system comprising:
an endoscope;
a moving device that holds and moves the endoscope; and
at least one processor,
wherein the at least one processor is configured to:
detect a movement direction of the endoscope moved by the moving device in a coordinate system of the moving device;
estimate an area of a moving body in an image captured by the endoscope;
detect a movement direction of an object in the image on the basis of another area in the image excluding the area of the moving body;
calculate a deviation between a coordinate system of the endoscope and the coordinate system of the moving device on the basis of the movement direction of the endoscope and the movement direction of the object; and
correct the coordinate system of the moving device on the basis of the calculated deviation.

2. The endoscope system according to claim 1, wherein the moving device holds the endoscope so as to allow rotation about a longitudinal axis of the endoscope, and the deviation between the coordinate system of the endoscope and the coordinate system of the moving device includes a deviation in a rotational direction about an axis corresponding to the longitudinal axis.

3. The endoscope system according to claim 2, wherein the endoscope is an oblique-viewing endoscope having a long lens barrel and an operation part connected to the proximal end of the lens barrel and holding an imaging device, the operation part being rotatable about a longitudinal axis of the lens barrel with respect to the lens barrel, and
the at least one processor is configured to calculate, as the deviation, a rotation angle of the endoscope about the longitudinal axis with respect to the moving device and a rotation angle of the operation part about the longitudinal axis with respect to the lens barrel on the basis of the movement direction of the endoscope and the movement direction of the object.

4. The endoscope system according to claim 1, wherein the at least one processor is configured to:
detect a movement direction of the object in the other area; and
calculate the deviation on the basis of the movement direction of the endoscope and the movement direction of the object in the other area.

5. The endoscope system according to claim 4, wherein the at least one processor is configured to:
detect multiple movement directions at multiple positions in the other area; and
calculate the movement direction of the object from the multiple movement directions.

6. The endoscope system according to claim 5, wherein the at least one processor is configured to:
count the number of the movement directions for each direction;
select, from the multiple movement directions, movement directions that are present in the largest number and movement directions close to the movement directions that are present in the largest number; and calculate the movement direction of the object from the selected movement directions.

7. The endoscope system according to claim 1, wherein the at least one processor is configured to:

detect a motion vector of the object in the other area; and calculate the deviation on the basis of the movement direction of the endoscope and the motion vector of the object in the other area.

8. The endoscope system according to claim 7, wherein the at least one processor is configured to:

detect multiple motion vectors at multiple positions in the other area; and calculate the motion vector of the object from the multiple motion vectors.

9. The endoscope system according to claim 8, wherein the at least one processor is configured to:

count the number of the motion vectors for each direction;

select, from the multiple motion vectors, motion vectors that are present in the largest number and motion vectors whose direction is close to the direction of the motion vectors that are present in the largest number; and calculate the motion vector of the object from the selected motion vectors.

10. The endoscope system according to claim 7, wherein the endoscope is an oblique-viewing endoscope having a long lens barrel and an operation part connected to the proximal end of the lens barrel and holding an imaging device, the operation part being rotatable about a longitudinal axis of the lens barrel with respect to the lens barrel, and the at least one processor is configured to:

acquire three-dimensional position information of the object in the image; and detect a three-dimensional motion vector from the three-dimensional position information.

11. The endoscope system according to claim 10, wherein the endoscope is configured to acquire a stereo image as the image, and the at least one processor is configured to acquire the three-dimensional position information from the stereo image.

12. The endoscope system according to claim 1, further comprising a user interface that receives input of a trigger from a user, wherein the at least one processor is configured to perform processing for correcting the coordinate system of the moving device in response to reception of the trigger at the user interface.

13. The endoscope system according to claim 12, wherein the at least one processor is configured to detect the movement direction of the object on the basis of at least two images captured at different times, and one of the at least two images is an image at a time when the trigger is received.

14. The endoscope system according to claim 12, wherein the at least one processor is configured to:

acquire an image captured by the endoscope at a predetermined time interval; and, each time the processor newly acquires an image, detect the movement direction of the object on the basis of the newly acquired image and a previously acquired image.

15. The endoscope system according to claim 1, wherein the at least one processor is configured to:

detect a motion vector of the object; and, when a magnitude of the motion vector of the object is greater than or equal to a predetermined threshold, calculate the deviation and corrects the coordinate system of the moving device.

16. The endoscope system according to claim 1, wherein the at least one processor is configured to:

perform, on the image, enhancement processing for enhancing a feature of the object; and detect the movement direction of the object from the image that has gone through the enhancement processing.

17. The endoscope system according to claim 1, wherein the at least one processor is configured to detect the movement direction of the object on the basis of the other area excluding an area obtained by adding a margin to the area of the moving body.

18. The endoscope system according to claim 1, wherein the at least one processor is configured to:

estimate motion vectors at respective positions in the image; and estimate the area of the moving body on the basis of the motion vectors at the respective positions.

19. An endoscope system comprising:

an endoscope;

a moving device that holds and moves the endoscope; and at least one processor, wherein the at least one processor is configured to:

detect a movement direction of the endoscope moved by the moving device in a coordinate system of the moving device;

estimate motion vectors at respective positions in an image captured by the endoscope;

detect a movement direction of an object in the image on the basis of another area in the image excluding an area in which magnitudes of the motion vectors are greater than or equal to a predetermined threshold;

calculate a deviation between a coordinate system of the endoscope and the coordinate system of the moving device on the basis of the movement direction of the endoscope and the movement direction of the object; and correct the coordinate system of the moving device on the basis of the calculated deviation.

20. A coordinate system correction method for correcting a coordinate system of a moving device that holds and moves an endoscope, the method comprising:

detecting a movement direction of the endoscope moved by the moving device in the coordinate system of the moving device;

estimating an area of a moving body in an image captured by the endoscope;

detecting a movement direction of an object in the image on the basis of another area in the image excluding the area of the moving body;

calculating a deviation between a coordinate system of the endoscope and the coordinate system of the moving device on the basis of the movement direction of the endoscope and the movement direction of the object; and correcting the coordinate system of the moving device on the basis of the calculated deviation.

* * * * *